(12) United States Patent
Cheong et al.

(10) Patent No.: US 8,563,696 B2
(45) Date of Patent: Oct. 22, 2013

(54) ANTIBODY SPECIFICALLY BINDING TO C-MET

(75) Inventors: Kwang-ho Cheong, Seongnam-si (KR); Sang-hyun Paek, Seoul (KR)

(73) Assignee: Samsung Electronics Co., Ltd., Suwon-si (KR)

(*) Notice: Subject to any disclaimer, the term of this patent is extended or adjusted under 35 U.S.C. 154(b) by 270 days.

(21) Appl. No.: 12/907,604

(22) Filed: Oct. 19, 2010

(65) Prior Publication Data

US 2011/0104176 A1    May 5, 2011

(30) Foreign Application Priority Data

Oct. 30, 2009    (KR) ........................ 10-2009-0104423

(51) Int. Cl.
  C07K 16/28    (2006.01)
  C07K 16/00    (2006.01)
  A61K 39/395   (2006.01)
  C12N 5/20     (2006.01)

(52) U.S. Cl.
  USPC ................ 530/388.22; 530/388.1; 530/387.1; 424/143.1; 424/141.1; 424/130.1; 435/810; 435/326

(58) Field of Classification Search
  None
  See application file for complete search history.

(56) References Cited

U.S. PATENT DOCUMENTS

| | | | |
|---|---|---|---|
| 5,571,509 | A | 11/1996 | Comoglio et al. |
| 5,646,036 | A | 7/1997 | Schwall et al. |
| 5,648,273 | A | 7/1997 | Bottaro et al. |
| 5,686,292 | A | 11/1997 | Schwall et al. |
| 6,214,344 | B1 | 4/2001 | Schwall et al. |
| 6,468,529 | B1 | 10/2002 | Schwall et al. |
| 7,498,420 | B2 | 3/2009 | Michaud et al. |
| 7,556,804 | B2 | 7/2009 | Prat |
| 2004/0166544 | A1 | 8/2004 | Morton et al. |
| 2005/0054019 | A1 | 3/2005 | Michaud et al. |
| 2005/0233960 | A1 | 10/2005 | Kong-Beltran et al. |
| 2006/0134104 | A1 | 6/2006 | Dennis et al. |
| 2006/0270594 | A1 | 11/2006 | Kong-Beltran et al. |
| 2007/0098707 | A1 | 5/2007 | Kong-Beltran et al. |
| 2008/0044415 | A1 | 2/2008 | Schwall et al. |
| 2009/0148457 | A1 | 6/2009 | Schwall et al. |
| 2009/0175860 | A1 | 7/2009 | Stover et al. |
| 2009/0209733 | A1 | 8/2009 | Otsuka et al. |
| 2009/0285807 | A1 | 11/2009 | Comoglio et al. |

FOREIGN PATENT DOCUMENTS

| | | |
|---|---|---|
| EP | 1997511 A1 | 12/2008 |
| EP | 2014681 A1 | 1/2009 |
| KR | 1020080113218 A | 12/2008 |
| KR | 1020090013745 A | 2/2009 |
| WO | 02/26917 A1 | 4/2002 |
| WO | 2006015371 A2 | 2/2006 |
| WO | 2007/090807 A1 | 8/2007 |
| WO | 2007/119447 A1 | 10/2007 |
| WO | 2007126799 A2 | 11/2007 |
| WO | 2009007427 A2 | 1/2009 |

OTHER PUBLICATIONS

Rudikoff et al. (Proc Natl Acad Sci USA 1982 vol. 79 p. 1979).*
MacCallum et al. J. Mol. Biol. (1996) 262, 732-745.*
Pascalis et al. (The Journal of Immunology (2002) 169, 3076-3084).*
Casset et al. (BBRC 2003, 307:198-205).*
Vajdos et al. (J. Mol. Biol. (2002) 320, 415-428).*
Chen et al. (J. Mol. Bio. (1999) 293, 865-881).*
Wu et al. (J. Mol. Biol. (1999) 294, 151-162).*
Padlan et al. (PNAS 1989, 86:5938-5942).*
Lamminmaki et al. (JBC 2001, 276:36687-36694).*
Tseng, J.R. et al., Preclinical efficacy of the c-Met inhibitor CE-355621 in a U87 MG mouse xenograft model evaluated by 18F-FDG small-animal PET, J Nucl Med. 2008; 49(1):129-134.
European Search Report for Application No. 10189420.2 dated Feb. 11, 2011.
Baselga et al., "Novel anticancer targets: revisiting ERBB2 and discovering ERBB3," *Nature*, 9: 463*-475 (2009).
Cooper et al., "Molecular cloning of a new transforming gene from a chemically transformed human cell line," *Nature*, 311 (6): 29-33 (1984).
Karamouzis et al., "Targeting MET as a strategy to overcome crosstalk-related resistance to EGFR inhibitors," *Lancet Oncology*, 10: 709-717 (2009).
Kong-Beltran et al., "The Sema domain of Met is necessary for receptor dimerization and activation," *Cancer Cell*, 6: 75-84 (2004).
Ma et al., "Functional Expression and Mutations of c-Met and Its Therapeutic Inhibition with SU11274 and Small Interfering RNA in Non—Small Cell Lung Cancer," *Cancer Research*, 65(4): 1479-1488 (2005).
Michieli et al., "Targeting the tumor and its microenvironment by a dual-function decoy Met receptor," *Cancer Cell*, 6: 61-73 (2004).
Park et al., "Mechanism of met Oncogene Activation," *Cell*, 45: 895-904 (1986).
Ridgway et al., "'Knobs-into-holes' engineering of antibody CH3 domains for heavy chain heterodimerization," *Protein Engineering*, 9(7): 617-621 (1996).

* cited by examiner

*Primary Examiner* — Sharon Wen
(74) *Attorney, Agent, or Firm* — Leydig, Voit & Mayer, Ltd.

(57) ABSTRACT

Antibodies specifically binding to c-Met protein, hybridoma cell lines, and compositions comprising the antibodies are disclosed herein. Methods of making and using the antibodies and compositions are also disclosed.

13 Claims, 8 Drawing Sheets

** p < 0.01 vs PBS

SEQUENCE LISTING

```
<160> NUMBER OF SEQ ID NOS: 10

<210> SEQ ID NO 1
<211> LENGTH: 5
<212> TYPE: PRT
<213> ORGANISM: Artificial Sequence
<220> FEATURE:
<223> OTHER INFORMATION: heavy chain CDR1 of monoclonal antibody AbF46

<400> SEQUENCE: 1

Asp Tyr Tyr Met Ser
1               5

<210> SEQ ID NO 2
<211> LENGTH: 19
<212> TYPE: PRT
<213> ORGANISM: Artificial Sequence
<220> FEATURE:
<223> OTHER INFORMATION: heavy chain CDR2 of monoclonal antibody AbF46

<400> SEQUENCE: 2

Phe Ile Arg Asn Lys Ala Asn Gly Tyr Thr Thr Glu Tyr Ser Ala Ser
  1               5                  10                  15

Val Lys Gly

<210> SEQ ID NO 3
<211> LENGTH: 13
<212> TYPE: PRT
<213> ORGANISM: Artificial Sequence
<220> FEATURE:
<223> OTHER INFORMATION: heavy chain CDR3 of monoclonal antibody AbF46

<400> SEQUENCE: 3

Asp Asn Trp Phe Ala Tyr Trp Gly Gln Gly Thr Leu Val
  1               5                  10

<210> SEQ ID NO 4
<211> LENGTH: 117
<212> TYPE: PRT
<213> ORGANISM: Artificial Sequence
<220> FEATURE:
<223> OTHER INFORMATION: heavy chain variable region of monoclonal
      antibody AbF46

<400> SEQUENCE: 4

Glu Val Lys Leu Val Glu Ser Gly Gly Gly Leu Val Gln Pro Gly Gly
  1               5                  10                  15

Ser Leu Arg Leu Ser Cys Ala Thr Ser Gly Phe Thr Phe Thr Asp Tyr
             20                  25                  30

Tyr Met Ser Trp Val Arg Gln Pro Pro Gly Lys Ala Leu Glu Trp Leu
         35                  40                  45

Gly Phe Ile Arg Asn Lys Ala Asn Gly Tyr Thr Thr Glu Tyr Ser Ala
     50                  55                  60

Ser Val Lys Gly Arg Phe Thr Ile Ser Arg Asp Asn Ser Gln Ser Ile
 65                  70                  75                  80

Leu Tyr Leu Gln Met Asp Thr Leu Arg Ala Glu Asp Ser Ala Thr Tyr
                 85                  90                  95
```

```
Tyr Cys Ala Arg Asp Asn Trp Phe Ala Tyr Trp Gly Gln Gly Thr Leu
            100                 105                 110

Val Thr Val Ser Ala
        115

<210> SEQ ID NO 5
<211> LENGTH: 17
<212> TYPE: PRT
<213> ORGANISM: Artificial Sequence
<220> FEATURE:
<223> OTHER INFORMATION: light chain CDR1 of monoclonal antibody AbF46

<400> SEQUENCE: 5

Lys Ser Ser Gln Ser Leu Leu Ala Ser Gly Asn Gln Asn Asn Tyr Leu
  1               5                  10                  15

Ala

<210> SEQ ID NO 6
<211> LENGTH: 7
<212> TYPE: PRT
<213> ORGANISM: Artificial Sequence
<220> FEATURE:
<223> OTHER INFORMATION: light chain CDR2 of monoclonal antibody AbF46

<400> SEQUENCE: 6

Trp Ala Ser Thr Arg Val Ser
  1               5

<210> SEQ ID NO 7
<211> LENGTH: 10
<212> TYPE: PRT
<213> ORGANISM: Artificial Sequence
<220> FEATURE:
<223> OTHER INFORMATION: light chain CDR3 of monoclonal antibody AbF46

<400> SEQUENCE: 7

Leu Thr Phe Gly Ala Gly Thr Lys Leu Glu
  1               5                  10

<210> SEQ ID NO 8
<211> LENGTH: 114
<212> TYPE: PRT
<213> ORGANISM: Artificial Sequence
<220> FEATURE:
<223> OTHER INFORMATION: light chain variable region of monoclonal
      antibody AbF46

<400> SEQUENCE: 8

Asp Ile Leu Met Thr Gln Ser Pro Ser Ser Leu Thr Val Ser Ala Gly
  1               5                  10                  15

Glu Lys Val Thr Met Ser Cys Lys Ser Ser Gln Ser Leu Leu Ala Ser
                 20                  25                  30

Gly Asn Gln Asn Asn Tyr Leu Ala Trp His Gln Gln Lys Pro Gly Arg
             35                  40                  45

Ser Pro Lys Met Leu Ile Ile Trp Ala Ser Thr Arg Val Ser Gly Val
         50                  55                  60

Pro Asp Arg Phe Ile Gly Ser Gly Ser Gly Thr Asp Phe Thr Leu Thr
 65                  70                  75                  80

Ile Asn Ser Val Gln Ala Glu Asp Leu Ala Val Tyr Tyr Cys Gln Gln
                 85                  90                  95

Ser Tyr Ser Ala Pro Leu Thr Phe Gly Ala Gly Thr Lys Leu Glu Leu
            100                 105                 110

Lys Arg
```

-continued

```
<210> SEQ ID NO 9
<211> LENGTH: 348
<212> TYPE: DNA
<213> ORGANISM: Artificial Sequence
<220> FEATURE:
<223> OTHER INFORMATION: heavy chain variable region of monoclonal
      antibody AbF46

<400> SEQUENCE: 9
gaggtgaagc tggtggagtc tggaggaggc ttggtacagc ctgggggttc tctgagactc      60
tcctgtgcaa cttctgggtt caccttcact gattactaca tgagctgggt ccgccagcct     120
ccaggaaagg cacttgagtg gttgggtttt attagaaaca aagctaatgg ttacacaaca     180
gagtacagtg catctgtgaa gggtcggttc accatctcca gagataattc ccaaagcatc     240
ctctatcttc aaatggacac cctgagagct gaggacagtg ccacttatta ctgtgcaaga     300
gataactggt ttgcttactg gggccaaggg actctggtca ctgtctct                  348

<210> SEQ ID NO 10
<211> LENGTH: 312
<212> TYPE: DNA
<213> ORGANISM: Artificial Sequence
<220> FEATURE:
<223> OTHER INFORMATION: light chain variable region of monoclonal
      antibody AbF46

<400> SEQUENCE: 10
gacattttga tgacccagtc tccatcctcc ctgactgtgt cagcaggaga gaaggtcact      60
atgagctgca agtccagtca gagtctttta gctagtggca accaaaataa ctacttggcc     120
tggcaccagc agaaaccagg acgatctcct aaaatgctga taattgggc atccactagg      180 gtatctggag tccctgatcg cttcataggc agtggatctg ggacggattt cactctgacc     240
atcaacagtg tgcaggctga agatctggct gtttattact gtcagcagtc ctacagcgct     300
ccgctcacgt tc                                                         312
```

ANTIBODY SPECIFICALLY BINDING TO C-MET

CROSS-REFERENCE TO RELATED APPLICATIONS

This application claims priority to Korean Patent Application No. 10-2009-104423, filed on Oct. 30, 2009, and all the benefits accruing therefrom under 35 U.S.C. §119, the disclosure of which is incorporated herein in its entirety by reference.

BACKGROUND

1. Field

The present disclosure relates to antibodies specifically binding to c-Met, fragments thereof, and a use of the antibodies.

2. Description of the Related Art

Hepatocyte growth factor (HGF) is a mesenchyme-derived pleitrophic cytokine that can induce mitogenesis, motogenesis, morphogenesis, and angiogenesis on various normal cells and tumor cells by binding to the extracellular region of a specific tyrosine kinase receptor, c-Met. Regulation of HGF/c-Met signaling pathway is implicated in various mechanisms related to cancer, such as tumor progression, metastasis, migration, invasion, and angiogenesis. In addition, c-Met amplification or mutation is thought to drive ligand-independent tumorogenesis. Thus, c-Met has recently emerged as a new target for anti-cancer therapy.

In particular, c-Met is known to be involved in induction of resistance to commonly used anti-cancer drugs, and thus, is regarded as an important player in personalized treatments. Representative anti-cancer drugs targeting epidermal growth factor receptor (EGFR) (ERBB1), such as Erbitux and Tarceva, work by blocking signal transduction related to a cancer development. Herceptin, which is a well-known breast cancer drug, targets ERBB2 (HER2) and works by blocking signal transduction necessary for cell proliferation. However, recent findings have indicated that among patients resistant to the drugs described above, anti-cancer drugs do not work due to overexpression of c-Met and activation of other types of signal transduction that leads to cell proliferation. Thus, many pharmaceutical firms are developing anti-cancer drugs to inhibit c-Met.

The related art discloses therapeutic antibody drugs that bind to c-Met to inhibit signal transduction that leads to cancer development.

Monoclonal antibodies against c-Met have been developed to prevent the interaction between the receptor and its cognate ligand, HGF. However, binding of these antibodies to c-Met induces dimerization of the receptor, and therefore, the antibodies have tended to have agonistic rather than antagonistic properties. This is due to the bivalent structure of the immunoglobulins, which act as natural dimerizing agents for the tyrosine kinase receptors. A 'one-armed' antagonistic antibody against c-Met has been described that consists of a monovalent Fab fragment with murine variable domains for the heavy and light chains fused to human IgG$_1$ constant domains. The antibody is prepared through a genetic recombinant method, and is currently in clinical trial. However, this antibody is effective only when the treatment is performed in combination with chemotherapy; when the antibody is used as a single agent, anti-cancer effects are relatively low. Therefore, despite significant advancement in treatment of cancer, there is still a need to develop new therapeutic antagonistic antibodies against c-Met.

SUMMARY

Provided are antibodies specifically binding to the extracellular region of c-Met protein, or antigen binding fragments thereof. In an embodiment, the antibody includes a heavy chain variable region comprising at least one heavy chain complementarity determining region (CDR) amino acid sequence selected from the group consisting of SEQ ID NO:1, SEQ ID NO:2, and SEQ ID NO:3; and a light chain variable region comprising at least one light chain CDR amino acid sequence selected from the group consisting of SEQ ID NO:5, SEQ ID NO:6, and SEQ ID NO:7.

Provided is a hybridoma cell having Accession Number KCLRF-BP-00220.

Provided are polynucleotides encoding a heavy chain variable region or a light chain variable region of an antibody specifically binding to the extracellular region of c-Met protein. In an embodiment, an isolated polynucleotide encoding an antibody heavy chain variable region has the amino acid sequence of SEQ ID NO: 4. In an embodiment, an isolated polynucleotide encoding an antibody light chain variable region has the amino acid sequence of SEQ ID NO: 8.

Provided are recombinant vectors including a polynucleotide that encodes a light chain variable region and/or a polynucleotide that encodes a heavy chain variable region of an antibody specifically binding to the extracellular region of c-Met protein and host cells transformed with the recombinant vectors. Methods of producing an antibody specifically binding to the extracellular region of c-Met protein by culturing the host cells are also disclosed.

Provided are compositions including an antibody specifically binding to the extracellular region of c-Met protein. In an embodiment, the composition includes the antibody; and a pharmaceutically acceptable carrier.

Provided are methods of treating an angiogenesis-related disease or cancer in a subject, the method including administering to a subject having an angiogenesis-related disease or cancer a therapeutically effective amount of an antibody specifically binding to the extracellular region of c-Met protein or antigen binding fragments thereof.

Provided are methods of detecting c-Met protein in a sample. In an embodiment, the method includes contacting a sample with an antibody specifically binding to the extracellular region of c-Met protein under conditions such that the antibody binds to c-Met protein if present in the sample; and detecting antibody bound to c-Met protein.

BRIEF DESCRIPTION OF THE DRAWINGS

These and/or other aspects, advantages, and features of this disclosure will become more apparent and readily appreciated from the following description of exemplary embodiments, taken in conjunction with the accompanying drawings of which.

DETAILED DESCRIPTION

Figure 1:
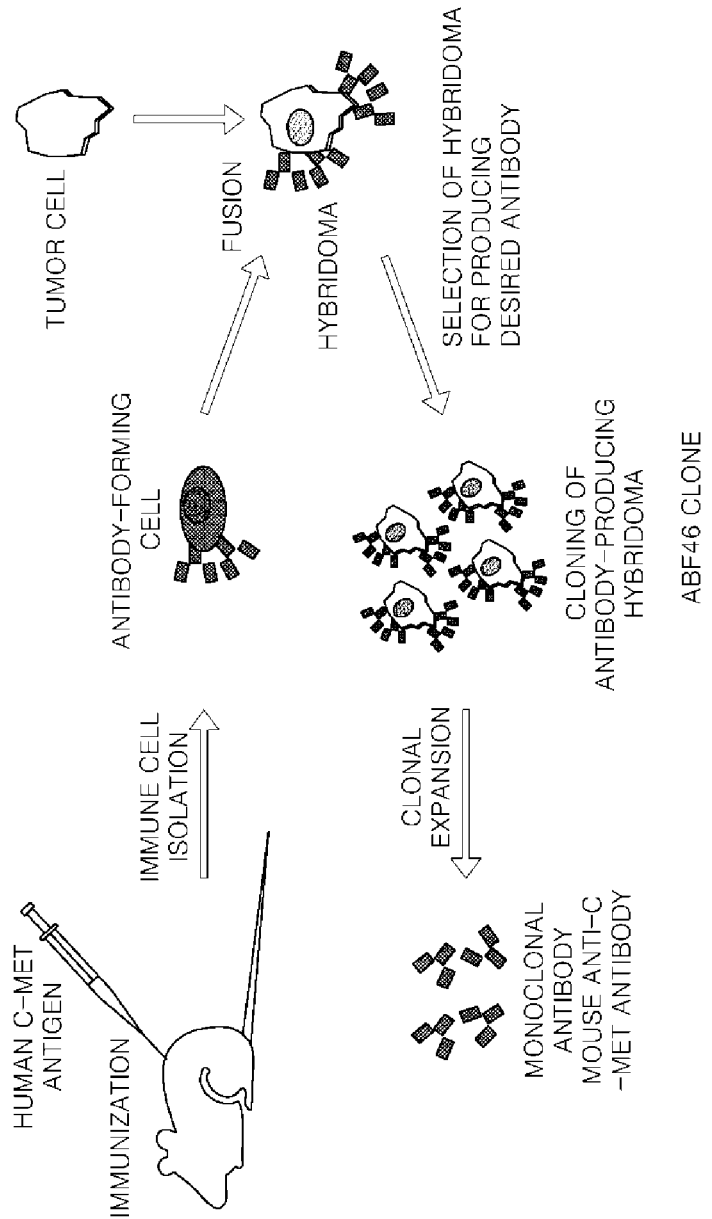
FIG. 1 is a schematic diagram illustrating a process of producing monoclonal antibody AbF46, according to an embodiment of the invention.

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description.

According to an embodiment of the present invention, there is provided a monoclonal antibody that is produced by a hybridoma cell having accession number of KCLRF-BP-00220, and that specifically binds an extracellular region of c-Met protein.

The term "c-Met" or "c-Met protein" refers to a receptor tyrosine kinase that binds to hepatocyte growth factor (HGF). The c-Met protein participates in various mechanisms, such as cancer development, metastasis, migration, invasion, and angiogenesis.

As used herein, the term "extracellular region" indicates, with respect to a transmembrane protein, the region of the protein exposed extracellularly.

In addition, the term "specifically binding" or "specifically recognized" herein means that an antibody exhibits appreciable affinity for an antigen and, preferably, does not exhibit significant crossreactivity. "Appreciable" binding affinity includes binding with an affinity of at least $10^6$ $M^{-1}$, specifically at least $10^7 M^{-1}$, more specifically at least $10^8$ $M^{-1}$, yet more specifically at least $10^9$ $M^{-1}$, or even yet more specifically at least $10^{10}$ $M^{-1}$. A binding affinity can also be indicated as a range of affinities, for example, $10^6$ $M^{-1}$ to $10^{10}$ $M^{-1}$, specifically $10^7 M^{-1}$ to $10^{10}$ $M^{-1}$, more specifically $10^8 M^{-1}$ to $10^{10}$ M. An antibody that "does not exhibit significant crossreactivity" is one that will not appreciably bind to an undesirable entity (e.g., an undesirable proteinaceous entity). An antibody specific for a particular epitope will, for example, not significantly crossreact with remote epitopes on the same protein or peptide. Specific binding can be determined according to any art-recognized means for determining such binding. In some embodiments, specific binding is determined according to Scatchard analysis and/or competitive binding assays.

The structure of a naturally occurring, intact antibody, or immunoglobulin, includes four polypeptides: two full-length light chains and two full-length heavy chains, with each light chain linked to a heavy chain by disulfide bonds. Each heavy chain has two regions, a constant region and a variable region. There are five isotypes for heavy chain constant regions, gamma (γ), mu (μ), alpha (α), delta (δ), or epsilon (ε), which can be further categorized by subtypes as gamma 1 (γ1), gamma 2 (γ2), gamma 3 (γ3), gamma 4 (γ4), alpha 1 (α1), or alpha 2 (α2). Similarly, each light chain has two regions, a constant region and a variable region. The light chain constant region is of either a kappa (κ) or lambda (λ) type. The variable regions differ in sequence among antibodies and are used in the binding and specificity of a given antibody to its particular antigen.

The term "monoclonal antibody" used herein refers to an antibody derived from a single cell clone. Monoclonal antibodies are monospecific antibodies that are identical to each other and possess binding specificity to a given antigen.

Hybridoma cells may be prepared using any method known in the art. For example, a hybridoma cell may be prepared by immunizing an animal with an immunogen, such as c-Met protein, fusing antibody-producing B cells derived from the immunized animal with myeloma cells to prepare hybridomas, and selecting a hybridoma cell that produces monoclonal antibodies that specifically bind the immunogen, such as c-Met protein. The animal immunized may be a mouse, a goat, a sheep, a guinea pig, a rat or a rabbit.

The immunization may be performed using any method known in the art. For example, mice can be immunized by emulsifying 1-100 μg of an immunogen, such as c-Met, with the same amount of an antigen adjuvant, such as a saline solution and/or Freund's adjuvant, and administering the mixture via subcutaneous or intraperitoneal injection 2 to 6 times at intervals between injections of 2 to 5 weeks. Next, 3 to 5 days after the final immunization of the mice, the spleen or lymphatic gland is taken out, and B cells from this tissue are fused with myeloma cells in the presence of a fusion facilitator, such as polyethylene glycol (PEG), using a method known in the art. The myeloma cells may be mouse-derived cells, such as P3U1, NS-1, P3×63. Ag 8.653, and Sp2/0-Ag14, or rat-derived cells, such as AG1 and AG2, but are not limited thereto. For example, the cell fusion technique may involve mixing B cells and myeloma cells at a ratio of 1:1 to 10:1, adding 10-80% of PEG having a molecular weight of 1,000 to 6,000, and incubating at a temperature of about 30° C. to about 37° C. for approximately 1 to 10 minutes. Hybridoma cells, which produce monoclonal antibodies that specifically bind to the extracellular region of c-Met, may be selected by culturing them in a selective medium, such as hypoxanthine, aminopterin, thymidine (HAT) medium, and measuring antibody activity in the hybridoma cell culture supernatant using an enzyme-linked immunosorbent assay (ELISA) method. Another method to select hybridoma cells that secrete monoclonal antibodies specific to the extracellular region of the c-Met proteins may involve a repetitive cloning technique, such as limiting dilutions.

The monoclonal antibody may be an $IgG_1$, $IgG_2$, $IgG_3$, $IgG_4$, IgM, IgE, $IgA_1$, $IgA_5$, or IgD-type antibody, for example, an $IgG_1$-type antibody. In addition, the light chain constant region of the monoclonal antibody may be of either A or K type. The c-Met protein used as an antigen may be derived from humans or mice.

According to an embodiment of the present invention, there is provided an antibody that has a heavy chain variable region including at least one heavy chain complementarity determining region (CDR) amino acid sequence selected from the group consisting of SEQ ID NO:1, SEQ ID NO:2, and SEQ ID NO:3, and a light chain variable region including at least one light chain CDR amino acid sequence selected from the group consisting of SEQ ID NO:5, SEQ ID NO:6, and SEQ ID NO:7, and specifically binds the extracellular region of c-Met protein. In some embodiments, the antibody is an antigen binding fragment thereof. In an embodiment, the heavy chain variable region comprises CDR amino acid sequences SEQ ID NO:1, SEQ ID NO:2, and SEQ ID NO:3. In an embodiment, the light chain variable region comprises CDR amino acid sequences SEQ ID NO:5, SEQ ID NO:6, and SEQ ID NO:7.

In an embodiment, the heavy chain variable region may have the amino acid sequence of SEQ ID NO:4, and the light chain variable region may have the amino acid sequence of SEQ ID NO:8.

The term "antibody" used herein includes intact antibodies as well as antigen binding fragments of intact antibody molecules, i.e., fragments having antibody-like specific binding to an antigen, for example, the extracellular region of c-Met.

The term "heavy chain" refers to a full-length heavy chain, comprising a variable region ($V_H$) that includes amino acid sequences that determine specificity for antigen binding and a constant region having three constant domains ($C_{H1}$, $C_{H2}$, and $C_{H3}$), and fragments thereof. The term "light chain" refers to a full-length light chain, comprising a variable region ($V_L$) that includes amino acid sequences that determine specificity for antigen binding and a constant region ($C_L$), and fragments thereof.

The term "complementarity determining region (CDR)" used herein refers to an amino acid sequence of an antibody variable region of a heavy chain or light chain. CDRs are necessary for antigen binding and determine the specificity of an antibody. Each variable region typically has three CDRs identified as CDR1 (CDRH1 or CDRL1, where "H" indicates the heavy chain CDR1 and L indicates the light chain CDR1), CDR2 (CDRH2 or CDRL2), and CDR3 (CDRH3 or CDRL3). The CDRs may provide contact residues that play a major role in the binding of antibodies to antigens or epitopes. Four framework regions, which have more highly conserved amino acid sequences than the CDRs, separate the CDR regions in the $V_H$ or $V_L$.

The term "antigen binding fragment(s)" used herein refers to fragments comprising portions of an intact antibody including some or all of the antigen binding regions and having the ability to bind specifically to the antigen of the intact antibody. For example, the antigen binding fragment may be a Fab fragment, a Fab' fragment, aF(ab')$_2$ fragment, a Fv fragment, or a scFv fragment, but is not limited thereto. A Fab fragment contains the variable region and the constant region of a light chain and a variable region and the first constant domain (CH1) of a heavy chain. A Fab fragment possesses one antigen binding site. A Fab' fragment is different from a Fab fragment in that Fab' additionally has the hinge region with at least one cysteine residue at the C-terminal end of CH1. A F(ab')$_2$ fragment comprises a pair of Fab fragments, which are generally covalently linked together by a disulfide bond between hinge cysteine residues near their carboxy termini. A Fv fragment is an antibody fragment which contains a complete antigen recognition and binding site, consisting of a dimer of one heavy and one light chain variable domain in tight association. Recombinant techniques for producing the Fv fragment are well-known in the art. A Fv fragment may have a structure in which the heavy chain and the light chain variable regions are linked by a non-covalent bond. Single-chain Fv (scFv) fragments generally may have a dimer structure in which the heavy chain and the light chain variable regions are covalently bound via a peptide linker whereas disulfide-linked (scFv)$_2$ fragments may have a structure in which two scFv fragments are directly linked to each other at the C-termini through a disulfide bond. The antigen binding fragment may be obtained using a protease to digest an intact antibody, such as papain to obtain Fab fragments or pepsin to obtain F(ab')$_2$ fragments. Alternatively, the antigen binding fragment may be prepared by a genetic recombinant technique.

The antibody may be a monoclonal antibody, a bispecific antibody, a non-human antibody, a humanized antibody, a human antibody, a chimeric antibody, a Fab fragment, a F(ab') fragment, a scFV fragment, a disulfide-bond Fv (sdFv) fragment, an anti-idiotype (anti-Id) antibody, and an epitope-binding fragment of these antibodies, but is not limited thereto.

The antibody may be a humanized antibody or a human antibody. A humanized form of a non-human antibody, such as a murine antibody, may be a chimeric antibody which contains minimal sequence derived from the non-human immunoglobulin, chains of the immunoglobulin, or fragments thereof, such as Fab, Fab', F(ab')$_2$, and Fv.

A non-human antibody is humanized using a method known in the art. In general, a humanized antibody has at least one amino acid residue introduced from a non-human donor. The humanization of a non-human antibody may be performed by replacing residues from a CDR of a human antibody with CDR residues from the antibody of the non-human species, such as mouse, rat, rabbit, or non-human primate, having the desired specificity, affinity, and capacity. In some instances, framework region (FR) residues of the human immunoglobulin are replaced by corresponding non-human residues.

A human antibody possesses an amino acid sequence which corresponds to that of an antibody produced by a human and/or has been made using any of the techniques for making human antibodies. Human antibodies may be produced using various techniques known in the art, such as phage display, genetic recombinant techniques, and/or cell engineering.

Effector regions of human antibodies may interact with complement and effector cells of the human immune system. In addition, the human immune system does not recognize human antibodies as foreign materials, and thus, the immune reaction against human antibodies introduced into a human may be significantly less severe than that against non-human and chimeric antibodies introduced into a human. Moreover, human antibodies have a long half-life in the blood stream, and therefore, dosage and frequency of administration may be reduced.

The term "chimeric antibody" used herein refers to an antibody with sequences derived from two different species.

The antibody specifically binding to the extracellular region of the c-Met protein, or the antigen binding fragment thereof, may include variants of the amino acid sequences disclosed herein within a range retaining the ability to bind specifically to the c-Met protein. For example, to enhance the binding affinity and/or other biological properties of the antibody, the amino acid sequences of the antibody may be mutated. For example, such mutations include deletion, insertion, and/or substitution of amino acid sequence residues of the antibody. The amino acid mutations are made based on relative similarity of properties of amino acid side chain substituents, for example, hydrophobicity, hydrophilicity, electric charge, and/or size. For example, arginine, lysine, and histidine are each positively-charged residues, alanine, glysine, and serine are similar in size, and phenylalanine, tryptophan, and tyrosine are similar in shape. Therefore, based on the considerations described above, arginine, lysine, and histidine may be biological functional equivalents, alanine, glycine, and serine may be biological functional equivalents, and phenylalanine, tryptophan, and tyrosine may be biological functional equivalents.

Amino acid substitutions in a protein, in which the activity of the molecules is not completely changed, are well-known in the art. Typical substitutions include Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and Asp/Gly substitutions. Considering mutations that lead to biologically equivalent activity, the antibody or the antigen binding fragment specifically binding to the extracellular region of the c-Met protein may also be understood to include amino acid sequences substantially similar to the sequences disclosed herein. In this regard, a substantially similar sequence may possess at least 60% homology, at least 70% homology, at least 80% homology, or at least 90% homology to the sequences described herein following maximum alignment of the sequences using a commonly used algorithm in the art. Alignment methods for sequence comparison are well-known in the art. For example, one of the sequence analysis programs available on the Internet at the NCBI Basic Local Alignment Search Tool (BLAST) home page, such as blastp, blastx, tblastn, and/or tblastx programs may be used.

According to an embodiment of the present invention, there is provided a polynucleotide encoding a heavy chain variable region of an antibody specifically binding the extracellular region of c-Met protein having an amino acid sequence of SEQ ID NO:4.

In another embodiment, an isolated polynucleotide encodes an antibody heavy chain variable region comprising at least one heavy chain complementarity determining region (CDR) amino acid sequence selected from the group consisting of SEQ ID NO: 1, SEQ ID NO: 2, and SEQ ID NO: 3.

The polynucleotide may have a nucleotide sequence of SEQ ID NO:9.

According to an embodiment of the present invention, there is provided a polynucleotide encoding a light chain variable region of an antibody specifically binding to the extracellular region of c-Met protein having an amino acid sequence of SEQ ID NO: 8.

In another embodiment, an isolated polynucleotide encodes an antibody light chain variable region comprising at least one light chain complementarity determining region (CDR) amino acid sequence selected from the group consisting of SEQ ID NO: 5, SEQ ID NO: 6, and SEQ ID NO: 7.

The polynucleotide may have a nucleotide sequence of SEQ ID NO: 10.

The term "polynucleotide" used herein refers to a polymer of deoxyribonucleotides or ribonucleotides that exists in either a single-stranded or a double-stranded form. The polynucleotide includes RNA and DNA (gDNA and cDNA) sequences as well as analogues of natural polynucleotides unless mentioned otherwise.

The polynucleotide also includes nucleotide sequences encoding the amino acid sequences of the heavy and light chain variable regions of the antibody specifically binding to the extracellular region of the c-Met protein and nucleotide sequences complementary thereto. The complementary sequences include completely complementary sequences and substantially complementary sequences that may hybridize with nucleotide sequences encoding amino acid sequences of the heavy and light chain variable regions of the antibody specifically binding to the extracellular region of the c-Met protein under stringent conditions known in the art. Specifically, stringent conditions mean, for example, hybridization to DNA in 6×SSC at about 45° C., followed by one or more washes in 0.2×SSC/0.1% SDS at about 50° C.-65° C.

In addition, nucleotide sequences encoding the amino acid sequences of the heavy and light chain variable regions may be mutated. The mutations include addition, deletion or substitution of nucleotides, and non-conservative or conservative substitution of amino acids. Polynucleotides encoding the amino acid sequences of the heavy and light chain variable regions of an antibody specifically binding to the extracellular region of the c-Met protein are understood to include nucleotide sequences substantially identical to the nucleotide sequences described above. These substantially identical nucleotide sequences may possess at least 80% homology, at least 90% homology, or at least 95% homology to the original nucleotide sequences following maximum sequence alignment using an algorithm known in the art. Examples of sequence analysis programs are available on the Internet at the NCBI Basic Local Alignment Search Tool (BLAST) home page, for example, blastn.

According to an embodiment of the present invention, there is provided a recombinant vector. In an embodiment, the recombinant vector comprises a polynucleotide encoding an antibody heavy chain variable region comprising at least one heavy chain complementarity determining region (CDR) amino acid sequence selected from the group consisting of SEQ ID NO: 1, SEQ ID NO: 2, and SEQ ID NO: 3; or a polynucleotide encoding an antibody light chain variable region comprising at least one light chain complementarity determining region (CDR) amino acid sequence selected from the group consisting of SEQ ID NO: 5, SEQ ID NO: 6, and SEQ ID NO: 7.

In an embodiment, the recombinant vector comprises a polynucleotide encoding a heavy chain variable region having an amino acid sequence of SEQ ID NO: 4 or a polynucleotide encoding a light chain variable region having an amino acid sequence of SEQ ID NO: 8. In some embodiments, the recombinant vector includes a polynucleotide encoding a heavy chain variable region having an amino acid sequence of SEQ ID NO: 4 and a polynucleotide encoding a light chain variable region having an amino acid sequence of SEQ ID NO: 8.

In some embodiments of the recombinant vector, the polynucleotide encoding a heavy chain variable region may have the nucleotide sequence of SEQ ID NO: 9, and the polynucleotide encoding a light chain variable region may have the nucleotide sequence of SEQ ID NO: 10.

The term "vector" used herein refers to a means, typically a polynucleotide, of transporting and expressing a target gene in a host cell. For example, the vector may include a plasmid vector, a cosmid vector, or a virus vector, such as a bacteriophage vector, an adenovirus vector, a retrovirus vector, and an adeno-associated virus vector. The recombinant vector may be prepared by manipulating a plasmid (i.e., pSC101, pGV1106, pACYC177, ColE1, pKT230, pME290, pBR322, pUC8/9, pUC6, pBD9, pHC79, pIJ61, pLAFR1, pHV14, pGEX series, pET series, and pUC19), a phage (i.e., λgt4λB, λ-Charon, λΔz1, and M13), or a virus (i.e., SV40) known in the art.

In the recombinant vector, a polynucleotide encoding amino acid sequences of the heavy and light chain variable regions may be operatively linked to a promoter. The term "operatively linked" refers to a functional linkage between a transcription regulating nucleotide sequence (for example, a promoter sequence) and other nucleotide sequences. Thus, the transcription regulating nucleotide sequence may regulate transcription and/or translation of other nucleotide sequences.

The recombinant vector may be constructed for cloning or expression. For example, a recombinant expression vector may be a vector known in the art for expressing foreign proteins in plants, animals or microorganisms. The recombinant vector may be constructed using various methods known in the art.

The recombinant vector may be constructed for use in prokaryotic or eukaryotic host cells. When a prokaryotic cell is used as the host cell, the expression vector generally includes a strong promoter capable of initiating transcription (i.e., $p_L^\lambda$ promoter, trp promoter, lac promoter, tac promoter, and T7 promoter), a ribosome binding site for initiating translation, and a transcription/translation termination sequence. When a eukaryotic cell is used as the host cell, the vector may contain an origin of replication, such as f1 origin of replication, SV40 origin of replication, pMB1 origin of replication, adeno origin of replication, AAV origin of replication, or BBV origin of replication, but is not limited thereto. A promoter in an expression vector for a eukaryotic host cell may be derived from a mammalian cell genome (i.e., a metallothionein promoter) or a mammalian virus (i.e., adenovirus late promoter, vaccinia virus 7.5K promoter, SV40 promoter, cytomegalovirus promoter, and tk promoter of HSV). A transcription termination sequence in an expression vector for a eukaryotic host cell is, in general, a polyadenylation sequence.

A vector system capable of expressing the heavy and light chain variable regions of the antibody may involve simultaneous expression of the heavy and light chain variable regions from a single vector, or independent expression of the heavy and light chain variable regions from separate vectors. In the latter system, two vectors may be introduced into the host cell by either co-transformation or targeted transformation.

According to an embodiment of the present invention, there is provided a host cell including a polynucleotide encoding a heavy chain variable region having an amino acid sequence of SEQ ID NO: 4 and a polynucleotide encoding a light chain variable region having an amino acid sequence of SEQ ID NO: 8.

The host cell may be transformed with a recombinant vector including a polynucleotide encoding a heavy chain variable region having an amino acid sequence of SEQ ID NO: 4 and polynucleotide encoding a light chain variable region having an amino acid sequence of SEQ ID NO: 8.

The host cell, which is capable of stably and continuously cloning or expressing the recombinant vector, may be any host cell known in the art. A prokaryotic host cell may be a *Bacillus* genus bacterium, such as *E. coli* JM109, *E. coli* BL21, *E. coli* RR1, *E. coli* LE392, *E. coli* B, *E. coli* X 1776, *E. coli* W3110, *Bacillus subtilis*, and *Bacillus thuringiensis*, an intestinal bacterium, such as *Salmonella typhimurium, Serratia marcescens*, or various *Pseudomonas* species bacterium. A eukaryotic host cell may be a yeast (*Saccharomyce cerevisiae*), an insect cell, a plant cell, or an animal cell, such as Sp2/0, CHO (Chinese Hamster Ovary) K1, CHO DG44, PER.C6, W138, BHK, COS-7, 293, HepG2, Huh7, 3T3, RIN, or a MDCK cell.

The polynucleotide or the recombinant vector including the same may be transferred into the host cell using a method known in the art. For example, when a prokaryotic cell is used as the host cell, the transfer may be performed using a $CaCl_2$ method or an electroporation method, and when a eukaryotic cell is used as the host cell, the transfer may be performed by microinjection, calcium phosphate precipitation, electroporation, liposome-mediated transfection, or gene bombardment, but is not limited thereto.

When a microorganism, such as *E. coli*, is used as the host cell, production is higher than that from an animal cell. However it is not suitable for producing intact Ig-type antibodies due to incorrect glycosylation of the antibodies produced, although microorganisms may be used for producing antigen binding fragments, such as Fab and Fv.

A transformed host cell may be selected using a phenotype expressed by a selectable marker by a method known in the art. For example, when the selectable marker is a specific antibiotic resistance gene, the transformed cells can be selected from a medium containing the antibiotic.

According to an embodiment of the present invention, there is provided a hybridoma (Accession Number: KCLRF-BP-00220) cell that produces a monoclonal antibody specifically binding to the extracellular region of c-Met protein.

An exemplary method of preparing the hybridoma cell will be described in detail below. The hybridoma cell prepared in the following Examples has been deposited in the Korean Cell Line Bank (Cancer Research Institute, Seoul National University College of Medicine, 28 Yongon-dong, Chongno-Gu, Seoul, 110-744, Korea), which is an international depository authority under the Budapest Treaty, as of 9 Oct. 2009 and received Accession Number KCLRF-BP-00220. The deposited hybridoma cell is kept according to the requirements of the Budapest Treaty for the deposit of a microorganism, and is available to the general public upon request with reference to the accession number.

According to an embodiment of the present invention, there is provided a composition for preventing or treating an angiogenesis-related disease or cancer. The composition includes an antibody that specifically binds the extracellular region of c-Met protein or an antigen binding fragment thereof disclosed herein; and a pharmaceutically acceptable carrier. The antibody or antigen binding fragment may be present in a therapeutically effective amount.

The composition may be used to prevent or treat cancer. Examples of cancer include carcinoma, lymphoma, blastoma, sarcoma, and leukemia. More specifically, cancer may be squamous cell carcinoma, small-cell lung cancer, non-small-cell lung cancer, adenocarcinoma of the lung, squamous cell carcinoma of the lung, peritoneal carcinoma, skin cancer, melanoma in the skin or eyeball, rectal cancer, cancer near the anus, esophagus cancer, small intestinal tumor, endocrine gland cancer, parathyroid cancer, adrenal cancer, soft-tissue sarcoma, urethral cancer, chronic or acute leukemia, lymphocytic lymphoma, hepatoma, gastrointestinal cancer, pancreatic cancer, glioblastoma, cervical cancer, ovarian cancer, liver cancer, bladder cancer, hepatocellular adenoma, breast cancer, colon cancer, large intestine cancer, endometrial carcinoma or uterine carcinoma, salivary gland tumor, kidney cancer, prostate cancer, vulvar cancer, thyroid cancer, or various types of head and neck cancers, but is not limited thereto.

In addition, the composition may be used to prevent or treat angiogenesis-related diseases. Angiogenesis is a physiological process that involves formation of new capillary vessels from pre-existing vessels. If angiogenesis is not controlled autonomously, the vessels grow abnormally, causing disease. Examples of angiogenesis-related diseases are rheumatoid arthritis, osteoarthritis, septic arthritis, psoriasis, corneal ulcer, age-related macular degeneration, diabetic retinopathy, proliferative vitreoretinopathy, premature retinopathy, keratoconus, Sjogren's syndrome, myopia ocular tumors, corneal graft rejection, abnormal wound healing, bone diseases, proteinuria, abdominal aortic aneurysm diseases, degenerative cartilage loss due to traumatic joint damage, nervous system demyelination diseases, liver cirrhosis, glomerular disease, premature rupture of embryonic membranes, inflammatory bowel disease, periodontal disease, arteriosclerosis, restenosis, central nervous system inflammation diseases, Alzheimer's disease, skin aging, and cancer invasion and metastasis, but are not limited thereto.

The antibody or antigen binding fragment thereof may specifically bind to the extracellular region of c-Met protein and include a heavy chain variable region having at least one heavy chain CDR amino acid sequence selected from the group consisting of SEQ ID NO: 1, SEQ ID NO: 2, and SEQ ID NO: 3 and a light chain variable region having at least one light chain CDR amino acid sequence selected from the group consisting of SEQ ID NO: 5, SEQ ID NO: 6, and SEQ ID NO: 7.

In some embodiments, the antibody that specifically binds to the extracellular region of the c-Met protein may be a monoclonal antibody produced from the hybridoma cell line having accession number KCLRF-BP-00220.

The antibody or antigen binding fragment thereof may act as an antagonist with respect to the c-Met protein.

The term "antagonist" is used in the broadest sense herein, and is understood to include all molecules that partially or entirely block, inhibit, and/or neutralize at least one biological activity of their target (e.g., c-Met). For example, the term "antagonist antibody" refers to an antibody that inhibits or decreases the biological activity of an antigen, for example c-Met, that the antibody binds. In some embodiments, the antibody or the antigen binding fragment thereof specifically binds to the extracellular region of the c-Met protein to block signal transduction, thereby, for example, inhibiting proliferation of the target tumor cell. Thus, the antibody or the antigen binding fragment thereof may treat cancer. In addition, the antibody or the antigen binding fragment thereof may inhibit angiogenesis through the same mechanism described above. The treatment of cancer and the inhibition of angiogenesis by the antibody or the antigen binding fragment thereof may be performed independently or simultaneously.

The composition for preventing or treating cancer or angiogenesis-related diseases includes a pharmaceutically acceptable carrier, which is commonly used in formulation. The pharmaceutically acceptable carrier may be lactose, dextrose, sucrose, sorbitol, mannitol, starch, gum acacia, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and mineral oil, but is not limited thereto. The pharmaceutical composition may further include a lubricant, a wetting agent, a sweetener, a flavor enhancer, an emulsifying agent, a suspension agent, or a preservative.

The composition for preventing or treating cancer and/or angiogenesis-related diseases may be administered orally or parenterally. Parenteral administration may include intravenous injection, subcutaneous injection, muscular injection, intraperitoneal injection, endothelial administration, local administration, intranasal administration, intrapulmonary administration, and rectal administration. Since oral administration leads to digestion of protein or peptide, an active antibody must be coated or formulated in a pharmaceutical composition to prevent digestion. In addition, the composition may be equipped with targeting ability to home to specific cells upon administration.

A suitable dosage of the antibody for preventing or treating cancer and/or angiogenesis-related diseases may depend on many factors, such as formulation methods, administration methods, ages of patients, body weight, gender, pathologic conditions, diets, administration time, administration route, excretion speed, and reaction sensitivity. A desirable dose of the antibody may be in the range of about 0.001 to 100 mg/kg for an adult. The term "therapeutically effective amount" used herein refers to a sufficient amount used in preventing or treating cancer and/or angiogenesis-related diseases.

The composition may be formulated with a pharmaceutically acceptable carrier and/or an additive into a unit dosage form or a multiple dosage form by any method known in the art. The formulation may be a solution in oil or an aqueous medium, a suspension, a syrup, an emulsifying solution, an extract, powder, granules, a tablet, or a capsule, and may further include a dispersing or a stabilizing agent. In addition, the composition may be administered as an individual drug, or together with other drugs, and may be administered sequentially or simultaneously with other drugs.

The composition includes the antibody or antigen binding fragments thereof, and thus, may be formulated as an immunoliposome, a liposome that includes as a targeting ligand an antibody-derived protein. The liposome containing the antibody may be prepared using any method known in the art. The immunoliposome is a lipid composition including phosphatidylcholine, cholesterol, and polyethyleneglycol-derived phosphatidylethanolamine, and may be prepared, for example, by a reverse phase evaporation method. For example, Fab' fragments may be adhered to the liposome through thiol-disulfide exchange. A chemical drug, such as doxorubicin, may also be included in the liposome.

According to an embodiment of the invention, there is provided a method of treating an angiogenesis-related disease or cancer of a subject, the method including administering to a subject having an angiogenesis-related disease or cancer a therapeutically effective amount of an antibody specifically binding to the extracellular region of c-Met protein, or an antigen binding antibody fragment. The antibody or antigen binding fragment thereof may be in the form of a composition including a pharmaceutically acceptable carrier.

The antibody or antigen binding fragment thereof may include a heavy chain variable region having at least one heavy chain CDR amino acid sequence selected from the group consisting of SEQ ID NO: 1, SEQ ID NO: 2, and SEQ ID NO: 3 and a light chain variable region having at least one light chain CDR amino acid sequence selected from the group consisting of SEQ ID NO: 5, SEQ ID NO: 6, and SEQ ID NO: 7.

A detailed description of the composition for preventing or treating cancer and/or angiogenesis-related diseases and the administration method thereof have been provided above.

The subjects to which the antibody is administered include animals. For example, the animals may be humans, dogs, cats, or mice.

According to an embodiment of the invention, there is provided an animal model for a cancer or an angiogenesis-related disease that is prepared by inoculating the animal with a c-Met expressing cancer cell line to form cancer therein, and in which, when an antibody specifically binding to the extracellular region of c-Met protein or antigen binding fragment thereof is administered to an individual, the angiogenesis or the formation or growth of tumor cells is inhibited. The antibody or antigen binding fragment thereof may be in the form of a composition including a pharmaceutically acceptable carrier.

Cancers formed in the animal model may be at least one selected from the group consisting of squamous cell carcinoma, small-cell lung cancer, non-small-cell lung cancer, adenocarcinoma of the lung, squamous cell carcinoma of the lung, peritoneal carcinoma, skin cancer, melanoma in the skin or eyeball, rectal cancer, cancer near the anus, esophagus cancer, small intestinal tumor, endocrine gland cancer, parathyroid cancer, adrenal cancer, soft-tissue sarcoma, urethral cancer, chronic or acute leukemia, lymphocytic lymphoma, hepatoma, gastrointestinal cancer, pancreatic cancer, glioblastoma, cervical cancer, ovarian cancer, liver cancer, bladder cancer, hepatocellular adenoma, breast cancer, colon cancer, large intestine cancer, endometrial carcinoma or uterine carcinoma, salivary gland tumor, kidney cancer, prostate cancer, vulvar cancer, thyroid cancer, and various types of head and neck cancers.

The tumor cells may be derived from the same or different species as those of the animal model. For example, the tumor cells may be U87-MG, a human glioblastoma cell line. The animal model may be any animal except for humans. The animal may be a mammal, such as a mouse. By using the animal model to test the efficacy of the treatment method, therapeutic effects of the antibody or the composition on treatment of cancer and angiogenesis-related diseases or cancer can be determined.

According to an embodiment of the present invention, a kit for diagnosing or detecting cancer is disclosed. The kit includes an antibody specifically binding to c-Met protein and can be used to measure the degree of expression of c-Met in a sample through an antigen-antibody binding reaction.

The c-Met protein is over-expressed in many kinds of cancers. In particular, it is known that most cancer cases in which the patients have a poor prognosis are characterized by over-expression of c-Met protein.

Examples of cancer that may be diagnosed or detected using the kit may include carcinoma, lymphoma, blastoma, and leukemia. More specifically, examples of cancer that may be diagnosed or detected may be bladder cancer, breast cancer, cervical cancer, cholangiocarcinoma, large intestine cancer, endometrial cancer, esophageal cancer, stomach cancer, head and neck cancer, kidney cancer, liver cancer, lung cancer, nasopharyngeal cancer, ovarian cancer, pancreatic cancer, gallbladder cancer, prostatic carcinoma, thyroid cancer, osteosarcoma, rhabdomyosarcoma, synovial sarcoma, Kaposi's sarcoma, leiomyosarcoma, malignant fibrous histiocytoma, fibrosarcoma, acute myeloid leukemia, adult T-cell leukemia, lymphoma, multiple myeloma, glioblastoma/astrocytoma, melanoma, mesothelioma, and Wilms' tumor, but the cancer is not limited thereto.

The kit may be used in diagnosing, staging, or detecting cancer by detecting c-Met protein through an antigen-antibody binding reaction, and may be a kit that may be used in any analysis method for detecting the presence of c-Met protein by interaction with an antibody disclosed herein. Kits are well-known to those of ordinary skill in the art, and may easily be re-configured by one of ordinary skill in the art to include appropriate reagents in addition to an antibody specifically binding to c-Met protein disclosed herein. For example, the kit may include an antibody, or antigen-binding fragment thereof, disclosed herein and a control cell in which c-Met protein is over-expressed. For example, the kit may be a kit for diagnosing or detecting cancer by immunohistochemistry, immunoblot, immunoprecipitation, ELISA, or radioimmunoassay (RIA), but is not limited thereto. The antibody may be any antibody specifically binding to c-Met protein disclosed herein.

The kit for diagnosing or detecting cancer may be prepared using any method known in the art. In some embodiments, the kit may include a freeze-dried antibody, a buffer solution, a stabilizing agent, and an inactive protein. A detailed description for detecting c-Met protein with the antibody, such as any method described herein, may be provided as a protocol included with the kit.

According to an embodiment of the invention, there is provided a method of detecting c-Met protein, the method includes contacting a sample isolated from a subject with an antibody specifically binding to c-Met protein. The method may provide information regarding c-Met expression level in the sample needed for diagnosis, staging, or detection of cancer.

The sample isolated from a subject may be a sample isolated from a patient with cancer or a normal person. In an embodiment, the sample may include tumor cells from a patient with cancer to assess the level of over-expression of c-Met protein in order to permit staging of the patient's cancer. In an embodiment, the sample is a cell or tissue isolated from a human to detect the presence or absence of cancer in the sample or to determine whether there is a risk of the development of the cancer in the sample.

In some embodiments, the cancer detected, staged or assessed for risk of development due to over-expression of c-Met protein is a cancer from the list disclosed above. The contacting may be performed by contacting the antibody specifically binding c-Met protein with the sample such that if the antigen c-Met protein exists in the sample the antibody will specifically bind the c-Met protein.

The antigen-antibody binding reaction may be detected using various immunoassay methods or immunostaining methods known in the art. Examples of immunoassay or immunostaining methods are radioimmunoassay, radioimmunoprecipitation, immunoprecipitation, ELISA, capture-ELISA, inhibition or competition assay, sandwich analysis, flow cytometry, immunofluorescence staining, and immunoaffinity purification, but are not limited thereto. For example, in an embodiment of a radioimmunoassay method, a radioisotope-labeled antibody may be used to detect c-Met protein. The radioisotope may be, for example, $C^{14}$, $I^{125}$, $P^{32}$ or $S^{35}$.

In an embodiment of an ELISA method, the method may include: (i) coating a surface of a solid substrate with a cell sample extract to be analyzed; (ii) incubating the cell sample extract with an antibody specifically binding to c-Met protein as a first antibody; (iii) incubating the resultant product with a secondary antibody conjugated to an enzyme; and (iv) measuring the activity of the enzyme.

The solid substrate may be a hydrocarbon polymer such as polystyrene or polypropylene, glass, a metal or a gel. For example, the solid substrate may be a microtiter plate. The enzyme conjugated to a secondary antibody may be an enzyme catalyzing a colorimetric, fluorometric, luminescence or infra-red reactions, but is not limited thereto. For example, the enzyme may be alkaline phosphatase, β-galactosidase, horseradish peroxidase, luciferase, or Cytochrome $P_{450}$. When alkaline phosphatase is used, bromo-chloro-indolyl-phosphate (BCIP), nitro blue tetrazolium (NBT), naphthol-AS-B1-phosphate, or enhanced chemifluorescence (ECF) may be used as a substrate. When horseradish peroxidase is used, chloronaphtol, aminoethylcarbazol, diaminobenzidine, D-luciferin, lucigenin (bis-N-methylacridinium nitrate), resorufin benzyl ether, luminol, Amplex Red reagent (10-acetyl-3,7-dihydroxyphenoxazine), hypersensitive reaction solution (HYR: p-phenylenediamine-HCl and pyrocatechol), tetramethylbenzidine (TMB), 2,2'-Azine-di[3-ethyl-benzthiazoline sulfonate] (ABTS), o-phenylenediamine (OPD) and naphtol/pyronin, glucose oxidase and t-nitroblue tetrazolium (t-NBT), or m-phenzaine methossulfate (m-PMS) may be used as a substrate.

The antibody specifically binding to c-Met protein may have a label generating a detectable signal. The label may be a chemical label such as biotin; an enzymatic label such as alkaline phosphatase, β-galactosidase, horseradish peroxidase and Cytochrome $P_{450}$; a radioactive label such as $C^{14}$, $I^{125}$, $P^{32}$ and $S^{35}$; a fluorescent label such as fluorescein; a luminescent label; a chemiluminescent label; or a fluorescence resonance energy transfer (FRET) label, but is not limited thereto.

The final measurement of enzyme activities or signals in the ELISA method may be performed by any method known to one skilled in the art to enable quantitative or qualitative analysis of c-Met protein amounts present in the sample. For example, signals could be detected easily by streptavidin in the case of a biotin-labeled antibody and by luciferin in the case of a luciferase-labeled antibody.

When an immunohistochemistry method is used, the method may include: (i) immobilizing a cell or tissue sample to be analyzed and sectioning thereof; (ii) incubating the section with an antibody specifically binding to c-Met protein as a first antibody; (iii) reacting the resultant product with a secondary antibody conjugated to an enzyme; and (iv) measuring the activity of the enzyme.

Methods for immobilizing and sectioning the sample are well known in the art. For example, the sample may be immobilized using a chemical material such as formalin. In addition, the section may be produced after the sample is embedded in a material such as paraffin. When paraffin is used in the production of the section, paraffinization may be performed to easily react an antigen in the cell or tissue sample with the first antibody. The operations (iii) and (iv) have already been described above with respect to the ELISA method.

The cancer may be diagnosed, staged, or detected by analyzing the intensity of the signals from the immunoassay indicating the presence of an antibody-c-Met protein complex. In other words, when, for example, the signal indicating the presence of an antibody-c-Met protein complex from a test sample is stronger than the corresponding signal from a normal control sample, the test sample may be determined to have higher expression of c-Met protein and therefore determined to have cancer present. Therefore the subject from whom the test sample was obtained may be diagnosed as having cancer.

One or more embodiments of the invention will now be described in further detail with reference to the following Examples. However, these examples are for illustrative purposes only and are not intended to limit the scope of the invention.

EXAMPLE 1

Preparation of Hybridoma Cells and Production of Monoclonal Antibody AbF46 Against c-Met The process of producing the hybridoma cell clones and obtaining monoclonal antibody, described below, is schematically illustrated in FIG. 1.

(1) Immunization of Mice

Five 4 to 6-week-old BALB/c mice (Japan SLC, Inc.) were each given an intraperitoneal injection of 0.100 μg of human c-Met/Fc fusion protein (R&D Systems, Inc.) emulsified in 0.2 mL complete Freund's adjuvant. After two weeks, each mouse were again administered an intraperitoneal injection of 50 μg human c-Met/Fc fusion protein emulsified with incomplete Freund's adjuvant. After one additional week, a final boosting with the antigen in incomplete Freund's adjuvant was performed. Blood was collected from the tail of each mouse three days after the final boosting to obtain serum, which was diluted at 1/1000 with phosphate buffered saline (PBS), and subjected to an enzyme-linked immunosorbent assay (ELISA) to determine the titer of antibodies recognizing c-Met. Mice in which a sufficient titer of the antibody was obtained were selected for performing cell fusion.

(2) Cell Fusion and Preparation of the Hybridoma Cells

A mixture of 50 μg human c-Met/Fc fusion protein in PBS was administered via an intraperitoneal injection to each mouse. After three days, each immunized mouse was anesthetized, and the spleen was then extracted and ground with a mesh to isolate cells, which were mixed with Dulbecco's Modified Eagle medium (DMEM) to prepare a spleen cell suspension. The suspension was centrifuged to collect the cell layer. Then, $1 \times 10^8$ spleen cells were mixed with $1 \times 10^8$ mouse myeloma cells (Sp2/0), and centrifuged to precipitate the cells. The precipitate was slowly dispersed, treated with 1 ml of 45% polyethylene glycol (PEG) in DMEM, and maintained at 37° C. for one minute before adding 1 ml of DMEM. After introducing an additional 10 ml of DMEM for 1 minute, the resultant was incubated in a water bath at 37° C. for 5 minutes. The total volume of the cell suspension was made to be 50 ml, and then was centrifuged. The resulting cell precipitate was re-suspended in an isolation medium, hypoxanthine aminopterin thymidine medium (HAT medium), at a concentration of $1-2 \times 10^5$ cells/ml and then distributed into a 96-well plate (0.1 ml per well), which was placed in a carbon dioxide incubator at 37° C. to prepare the hybridoma cells.

(3). Selection of the Hybridoma Cells that Produce Monoclonal Antibodies Against c-Met Protein The hybridoma cells prepared in (2) were screened by ELISA for production of antibodies with activity against human c-Met/Fc fusion protein and human Fc protein.

50 μl (2 ug/ml) of human c-Met/Fc fusion protein was coated on each well of a microtiter plate, and unreacted antigens were removed by washing. To exclude antibodies binding to Fc, and not to c-Met, human Fc protein was coated on each well of a different microtiter plate using the same method as above. Next, 50 μl of hybridoma cell suspension was added to each well of the microtiter plates to react for 1 hour. Then, the microtiter plates were washed with TRIS buffered saline-TWEEN 20 (TBST) solution. Goat anti-mouse IgG-horseradish peroxidase (IgG-HRP) was added to the wells, reaction was allowed to occur at room temperature for 1 hour, and then washing was performed with TBST solution to remove unreacted antibodies. Subsequently, a solution of o-phenylenediamine dihydrochloride (OPD), a substrate for colorimetric detection of peroxidase, was added to each well, and the degree of reaction was evaluated by measuring absorption at 450 nm using an ELISA reader. Through this method, hybridoma cell lines that produce antibodies highly specific to the human c-Met protein and not to the human Fc protein were repeatedly selected. A limiting dilution was performed on the selected hybridoma cell lines to obtain a single clone of hybridoma cell lines producing monoclonal antibodies. A selected hybridoma cell line producing a monoclonal antibody was named SAIT-MET-AbF46, and was deposited in the Korean Cell Line Bank and given accession number KCLRF-BP-00220.

(4) Production and Purification of the Monoclonal Antibody

The hybridoma cells obtained in (3) above were cultured in serum free medium to produce and purify the monoclonal antibodies.

First, AbF46 hybridoma cells cultured in 50 ml of culture medium (DMEM) with 10% fetal bovine serum (FBS) were centrifuged to obtain a cell precipitate, which was washed with 20 ml of PBS at least twice to remove FBS. Then, 50 ml of DMEM was introduced to re-suspend the cell precipitate, and the resultant was incubated in a carbon dioxide incubator at 37° C. for 3 days. After centrifugation to remove the antibody-producing cells, cell culture medium including the antibodies was isolated and stored at 4° C., or used directly. Antibodies were purified from 50 to 300 ml of the culture using an AKTA purification device (GE Health) equipped with an affinity column (protein G agarose column; Pharmacia, USA), and the purified antibodies were stored by replacing the supernatant with PBS using a filter for protein aggregation (Amicon).

An overview of the process to produce the monoclonal antibodies, as described in Example 1, is illustrated in FIG. 1.

EXAMPLE 2

Determination of the Monoclonal Antibody AbF46 Isotype

To determine the isotype of the antibody produced by the hybridoma cell line prepared in Example 1, an ELISA experiment was performed to check the presence of each murine antibody isotype using a BD Pharmingen kit (BD Biosciences) as follows. The results are summarized in Table 1 below. From the results, the monoclonal antibody AbF46 is determined to have the highest reactivity with anti-IgG$_1$ (i.e., 827.0), and its light chain was determined to be of κ type (Table 1).

TABLE 1

| mAb | IgA | IgE | IgG$_1$ | IgG$_{2a}$ | IgG$_{2b}$ | IgG$_3$ | IgM | Determination | Light chain |
|---|---|---|---|---|---|---|---|---|---|
| AbF46 | 5.0 | 43.5 | 827.0 | 6.0 | 11.0 | 3.0 | 4.0 | 827.0  IgG$_1$ | κ |

EXAMPLE 3

Determination of Reactivity of Monoclonal Antibody AbF46 to c-Met of Different Species ELISA was used to analyze whether the monoclonal antibody AbF46 against the human c-Met protein, prepared in Example 1, recognized the murine c-Met antigen. First, 50 μl of human and murine c-Met/Fc fusion proteins (R&D Systems) at a concentration of 2 ug/ml were added to separate wells of a microtitre plate, and uncoated antigens were removed by washing. Next, 50 ng of the purified monoclonal antibody AbF46 was added to each well and allowed to react for 1 hour. Then, washing was performed with TRIS buffered saline-TWEEN 20 (TBST) solution. Goat anti-mouse IgG-HRP was added thereto and allowed to react at room temperature for 1 hour, and the wells were washed with TBST solution. Afterwards, a peroxidase substrate solution (OPD) was introduced to each well, and the degree with peroxidase was evaluated by measuring the absorption at 450 nm using an ELISA reader to determine whether the monoclonal antibody AbF46 was bound to the human and/or the mouse c-Met protein. Results are shown in Table 2 below. For comparison, a commonly used monoclonal antibody against human c-Met, 5D5 (Genentech), was tested and displayed low reactivity to mouse c-Met. In contrast, monoclonal antibody AbF46 recognized both human and mouse c-Met proteins (Table 2). These results highlight the application potential of the monoclonal antibody AbF46 in animal experiments.

TABLE 2

| Antigen | 5D5 | AbF46 |
|---|---|---|
| human c-Met/Fc fusion protein | 0.3729 | 0.3793 |
| mouse c-Met/Fc fusion protein | 0.1126 | 0.3328 |

EXAMPLE 4

Affinity Measurement of the Monoclonal Antibody AbF46

Figure 2:
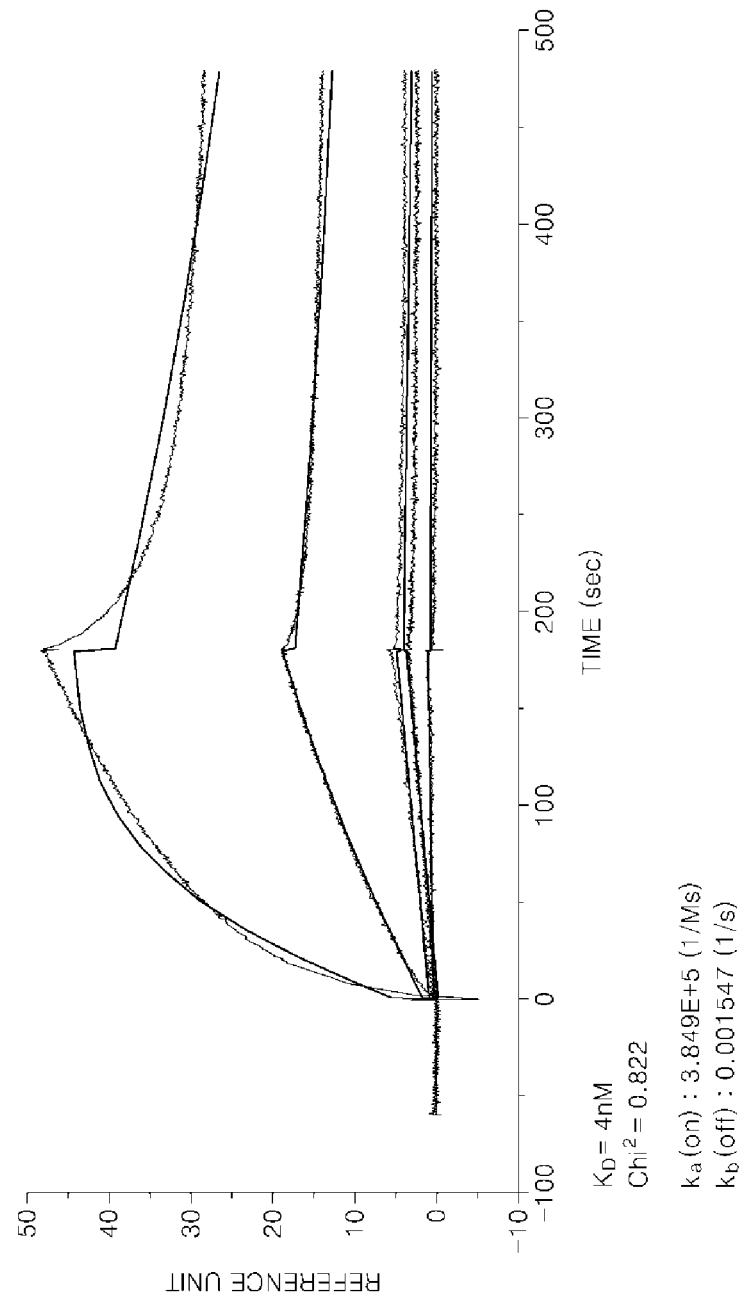
FIG. 2 is a graph showing the signal from a surface plasmon resonance experiment measuring binding affinity of monoclonal antibody AbF46 to human c-Met as a function of time, according to an embodiment of the invention.

A surface plasmon resonance (SPR) device (Biacore) was used to measure the binding affinity of the monoclonal antibody AbF46 prepared in Example 1 to human c-Met protein. The human c-Met protein was first immobilized on a CM5 chip, and the monoclonal antibody AbF46 was allowed to flow into a microfluidic chamber to obtain $k_a$ (on) and $k_b$ (off) values as illustrated in FIG. 2. Then, the $K_d$ value was calculated from the $k_a$ and $k_b$ values. The monoclonal antibody AbF46 was determined to have a $K_d$ value of 4 nM. In addition, the Chi$^2$ value, which represents the reliability of the experiment, was 0.822 (in a Biacore analysis method, a Chi$^2$ value of 1 or less indicates high reliability of the data). From these results, the monoclonal antibody AbF46 possesses high binding affinity to human c-Met protein. For reference, OA-5D5 antibody (Genentech's 'one-armed' antibody version of 5D5), which is in phase II clinincal trials, has a $K_d$ value of 8.27 nM.

EXAMPLE 5

Inhibitory Effects of Monoclonal Antibody AbF46 on Proliferation of Tumor Cells

In vitro cell proliferation analysis was performed using U87-MG cells, a human glioblastoma cell line, that produce HGF and express c-Met on the cell surface to determine anti-cancer effects of monoclonal antibody AbF46 on proliferation of tumor cells.

First, 100 μl of U87-MG cells suspended in 10% FBS/DMEM culture (5×10$^3$ cells/100 μl) were introduced to each well of a 96-well plate and incubated for 48 hours. After treatment with 50 ng/ml hepatocyte growth factor (HGF), cell suspensions were treated with 0 μg/ml, 5 μg/ml or 10 μg/ml of the monoclonal antibody AbF46, and incubated in DMEM media with 0.05% of FBS for 48 hours. Finally, the number of U87-MG cells was quantified by measuring absorption at 450 nm using a Cell Counting Kit-8 (CCK-8) (Dojindo Molecular Technologies, Inc.). HGF and AbF46 are not added to the control cells.

Figure 3A:
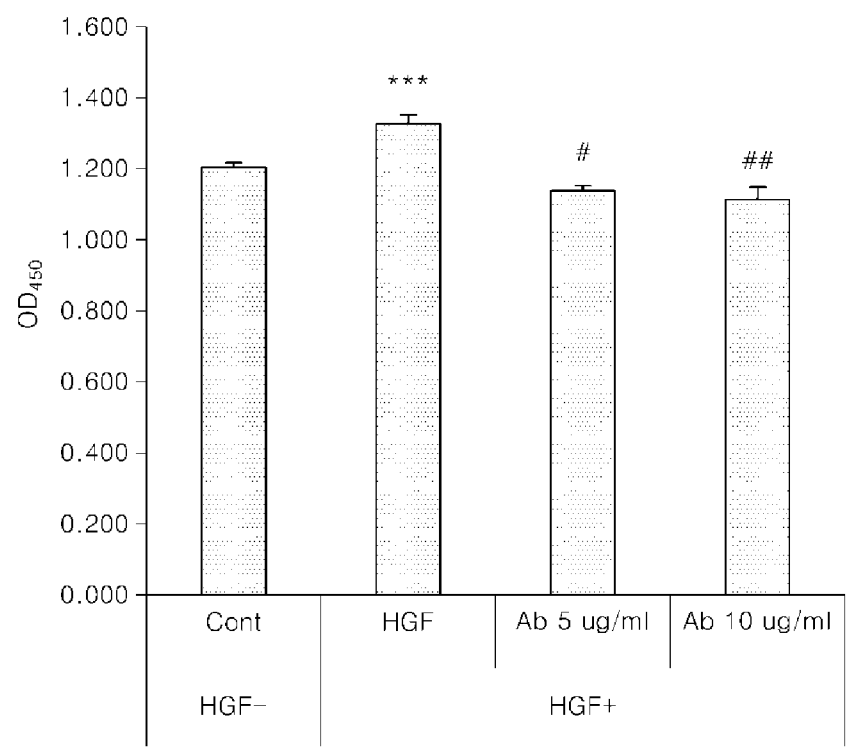
FIG. 3A is a histogram showing $OD_{450}$ of tumor cells grown in the absence (−) or presence (+) of HGF with 0, 5 or 10 μg/mL AbF46.
Figure 3B:
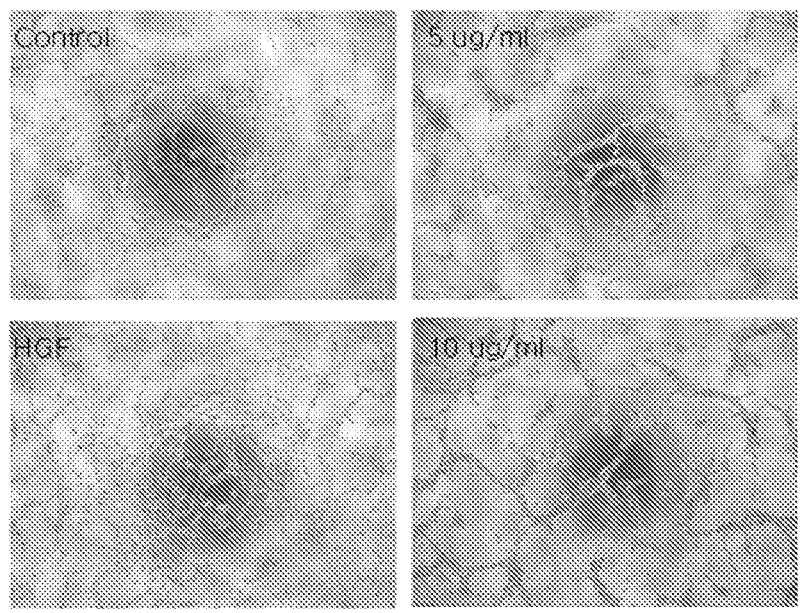
FIG. 3B presents images of U87-MG cells grown in the absence (control) or presence of HGF with 0, 5 or 10 μg/mL AbF46, according to an embodiment of the invention.

The results are illustrated in FIG. 3A and FIG. 3B. The monoclonal antibody AbF46 inhibits proliferation of tumor cells induced by HGF. Additionally, in other experiments monoclonal antibody AbF46 was shown to also inhibit proliferation of cells independent of HGF induction.

EXAMPLE 6

Inhibitory Effects of Monoclonal Antibody AbF46 on Angiogenesis

A tube formation assay using human umbilical vein endothelial cell (HUVEC) lines was performed with a BD Bio-Coat™ Angiogenesis System-Endothelial Cell Tube Formation kit (BD Biosciences) to determine anti-angiogenesis effects of monoclonal antibody AbF46. Tube formation is an indicator of angiogenesis.

Expression of c-Met is known to induce cancer proliferation and blood vessel formation around cancer. In the present experiment, tube formation following treatment with HGF was first observed, and the effects of monoclonal antibody AbF46 on tube formation were analyzed.

Figure 4A:
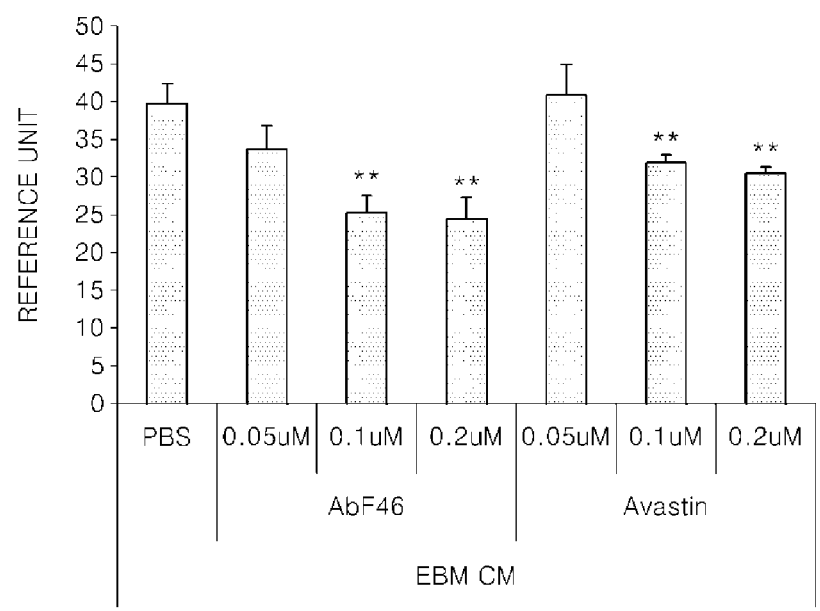
FIG. 4A is a histogram showing the inhibition of angiogenesis by monoclonal antibody AbF46 and the commercially available drug, AVASTIN.
Figure 4B:
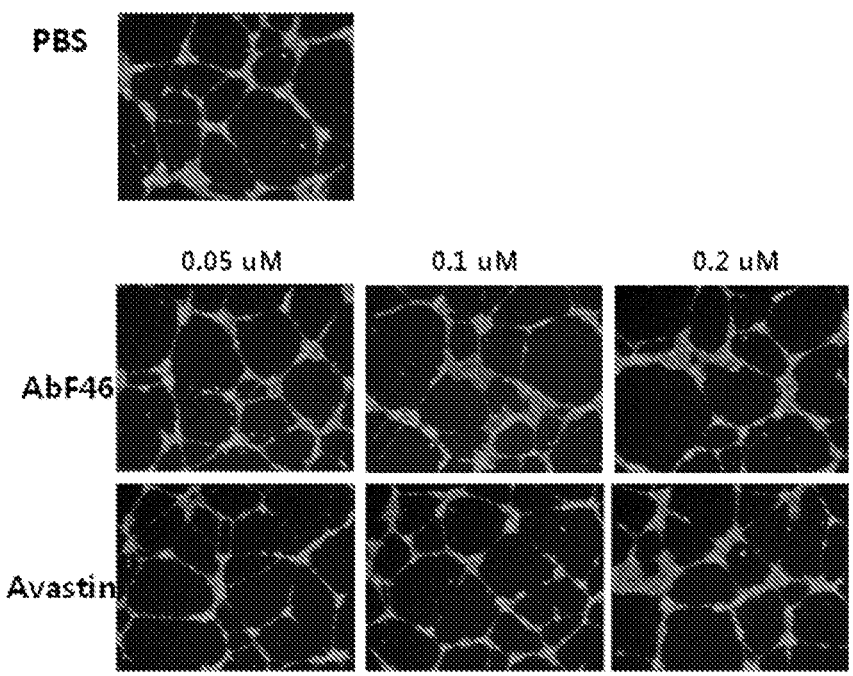
FIG. 4B presents images of results comparing inhibition of angiogenesis by monoclonal antibody AbF46 and the commercially available drug, AVASTIN.

FIG. 4A presents the tube formation index (reference unit) calculated by the length of tubes using BD BioCoat Angiogenesis System. Endothelial tube formation is measured using the MetaMorph Software system. As illustrated in FIG. 4A and FIG. 4B, when monoclonal antibody AbF46 was introduced, tube formation was significantly inhibited. In addition, when monoclonal antibody AbF46 was used in the same amount as AVASTIN (Genentech), a commercially available recombinant humanized monoclonal antibody that acts as an angiogenesis inhibitor, the monoclonal antibody AbF46 inhibited angiogenesis to a greater degree than AVASTIN.

EXAMPLE 7

Effects of Monoclonal Antibody AbF46 in a Cancer Animal Model

Experiments to monitor change in the size of tumor cells in a mouse xenograft model transplanted with U87-MG cells when monoclonal antibody AbF46 was administered in vivo were performed to determine in vivo anti-cancer effects of monoclonal antibody AbF46.

50 µl suspensions of human brain tumor U87-MG cells ($3\times10^6$ cells/50 µl) were administered via subcutaneous injection to 6 week-old magnetic BALB/c nude mice. After 4-5 weeks, 6 mice contracted with cancer were selected for each treatment group in the study. The monoclonal antibody AbF46 was administered via intraperitoneal injection to these mice 4-5 weeks after tumor cells were formed.

Figure 5A:
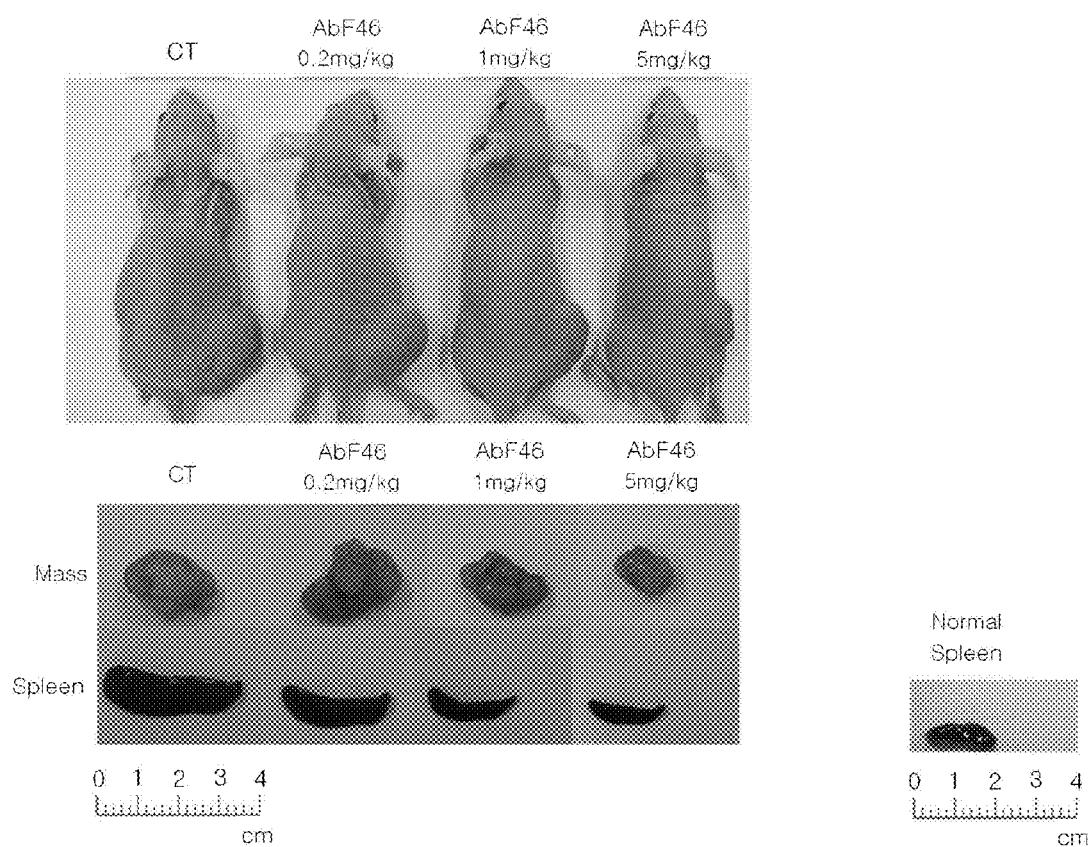
FIG. 5A presents photographic images showing decrease in tumor mass and spleen in vivo with increasing amounts of monoclonal antibody AbF46 administered to a mouse xenograft model transplanted with U87-MG cells, according to an embodiment of the invention.
Figure 5B:
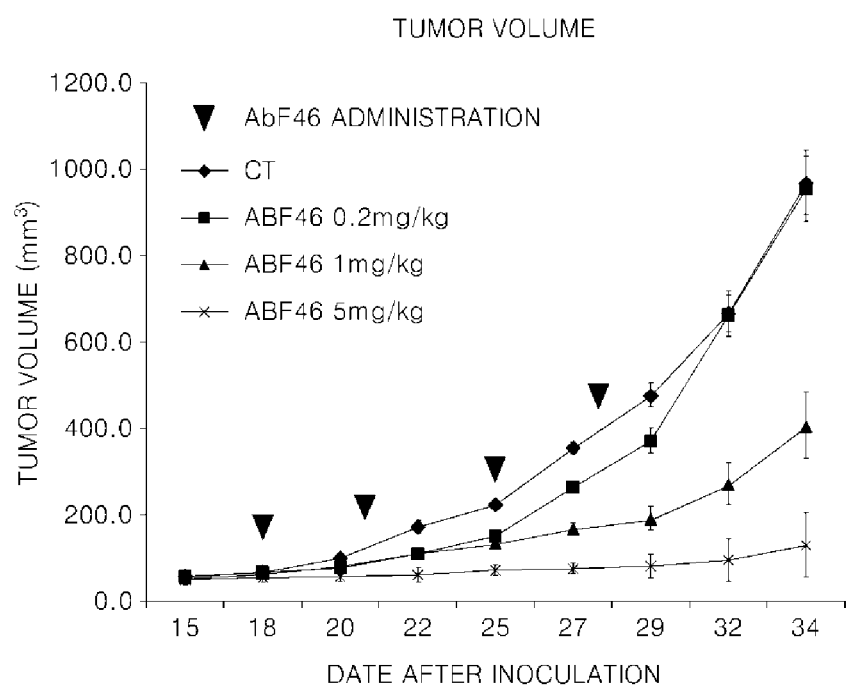
FIG. 5B is a graph showing increase in tumor volume in a mouse xenograft model transplanted with U87-MG cells as a function of time after inoculation with administration of various amounts of monoclonal antibody AbF46.

As illustrated in FIG. 5B, the monoclonal antibody AbF46 was administered via intraperitoneal injection 4 times to the mice over a 2 week period after formation of tumor cells. A concentration of 0.2 mg/kg did not have anti-cancer effects, but a concentration of 1 mg/kg significantly decreased the size of the tumor cells compared to the control. In addition, the size of the tumor at a concentration of 5 mg/kg was 10 times smaller than that of the control, and did not increase as time progressed.

In particular, as illustrated in FIG. 5A, the monoclonal antibody AbF46 also inhibited splenomegaly caused by a granulocyte-colony stimulating factor (G-CSF) known to be secreted from U87-MG cells upon formation of tumor cells. These results from a mouse model indicate that monoclonal antibody AbF46 participates in various mechanisms that inhibit the functions of c-Met without causing toxicity, and as a result, can lead to excellent anti-cancer effects in vivo.

EXAMPLE 8

CDR Amino Acid Sequences of Monoclonal Antibody AbF46

The heavy and the light chain CDR amino acid sequences of monoclonal antibody AbF46 produced in Example 1, which are essential for antigen recognition, are displayed in Table 3. These CDR amino acid sequences were confirmed to be novel amino sequences that are different from those of other antibodies known to recognize c-Met (SEQ ID Nos: 1-3 and SEQ ID Nos: 5-7).

TABLE 3

| | CDR1 | CDR2 | CDR3 |
|---|---|---|---|
| AbF46 heavy chain | DYYMS (SEQ ID NO: 1) | FIRNKANGYT TEYSASVKG (SEQ ID NO: 2) | DNWFAYWGQGTLV (SEQ ID NO: 3) |
| AbF46 light chain | KSSQSLLAS GNQNNYLA (SEQ ID NO: 5) | WASTRVS (SEQ ID NO: 6) | LTFGAGTKLE (SEQ ID NO: 7) |

As described above, according to one or more of the above embodiments of the present invention, there are provided an antibody specifically binding to c-Met and antigen binding fragments thereof, and compositions and kits including the antibody. Additionally, methods for preventing or treating an angiogenesis-related disease or cancer are disclosed, whereby the angiogenesis-related disease or cancer may be efficiently prevented or treated.

The terminology used herein is for the purpose of describing particular embodiments only and is not intended to be limiting of the invention. The terms "a" and "an" do not denote a limitation of quantity, but rather denote the presence of at least one of the referenced item. The terms "comprising", "having", "including", and "containing" are to be construed as open-ended terms (i.e. meaning "including, but not limited to"). The modifier "about" used in connection with a quantity is inclusive of the stated value and has the meaning dictated by the context (e.g., includes the degree of error associated with measurement of the particular quantity), Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

All methods described herein can be performed in a suitable order unless otherwise indicated herein or otherwise clearly contradicted by context. No language in the specification should be construed as indicating any non-claimed element as essential to the practice of the invention as used herein.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

It should be understood that the exemplary embodiments described therein should be considered in a descriptive sense only and not for purposes of limitation. Descriptions of features or aspects within each embodiment should typically be considered as available for other similar features or aspects in other embodiments.

What is claimed is:

1. A hybridoma cell deposited with the Korean Cell Line Research Foundation having Accession Number: KCLRF-BP-00220.

2. An isolated monoclonal antibody, produced from the hybridoma cell of claim 1, wherein the monoclonal antibody specifically binds to an extracellular region of c-Met protein.

3. The monoclonal antibody of claim 2, comprising an IgG1-type antibody.

4. The monoclonal antibody of claim 2, wherein the c-Met protein is human c-Met protein or mouse c-Met protein.

5. An antigen binding fragment of the monoclonal antibody of claim 2.

6. An isolated antibody that specifically binds to an extracellular region of c-Met protein, the antibody comprising
   a heavy chain variable region comprising heavy chain complementarity determining region (CDR) amino acid sequences SEQ ID NO:1, SEQ ID NO:2, and SEQ ID NO:3; and
   a light chain variable region comprising light chain CDR amino acid sequences SEQ ID NO:5, SEQ ID NO:6, and SEQ ID NO:7.

7. The antibody of claim 6, wherein the heavy chain variable region comprises an amino acid sequence of SEQ ID NO: 4, and the light chain variable region comprises an amino acid sequence of SEQ ID NO: 8.

8. The antibody of claim 6, wherein the antibody is an antigen-binding antibody fragment.

9. A composition comprising
   the antibody of claim 2; and
   a pharmaceutically acceptable carrier.

10. A composition comprising
    the antibody of claim 6; and
    a pharmaceutically acceptable carrier.

11. A kit comprising the antibody of claim 2.

12. A kit comprising the antibody of claim 6.

13. The antibody of claim 6, wherein the heavy chain variable region comprises amino acid sequences SEQ ID NO:1, SEQ ID NO:2, and SEQ ID NO:3; and
    the light chain variable region comprises amino acid sequences SEQ ID NO:5, SEQ ID NO:6, and residues 95-111 of SEQ ID NO:8.

* * * * *